United States Patent [19]
Wiley et al.

[11] 4,183,860
[45] * Jan. 15, 1980

[54] ANTIBIOTICS 7(S)-O-ALKYLNOGAROLS

[75] Inventors: Paul F. Wiley, Kalamazoo; David J. Houser, Portage, both of Mich.

[73] Assignee: The Upjohn Company, Kalamazoo, Mich.

[*] Notice: The portion of the term of this patent subsequent to Apr. 25, 1995, has been disclaimed.

[21] Appl. No.: 924,975

[22] Filed: Jul. 17, 1978

[51] Int. Cl.$^2$ .......................................... C07D 319/08
[52] U.S. Cl. ................................ 260/340.3; 424/181; 424/278
[58] Field of Search ...................................... 260/340.3

[56] References Cited

U.S. PATENT DOCUMENTS

| 3,183,157 | 5/1965 | Bhuyan et al. | 424/278 |
| 3,501,569 | 3/1970 | Wiley et al. | 424/119 |
| 4,086,245 | 4/1978 | Wiley et al. | 260/340.3 |

Primary Examiner—Ethel G. Love
Attorney, Agent, or Firm—Roman Saliwanchik

[57] ABSTRACT

Novel antibiotics, 7(S)—O—alkylnogarols, prepared by acidic alcoholysis of nogamycin, which are active against various microorganisms, for example, *Bacillus subtilis*, *Streptococcus pyogenes*, and *Mycobacterium avium*. Thus, they can be used to inhibit the growth of the above microorganisms in various environments.

6 Claims, No Drawings

ANTIBIOTICS 7(S)-O-ALKYNOGAROLS

The invention described herein was made in the course of, or under Contract NO1-CM-43753 with the National Cancer Institute, National Institutes of Health, Bethesda, Md. 20014.

BACKGROUND OF THE INVENTION

The known antibiotic nogalamycin, and a process for its preparation, are described in U.S. Pat. No. 3,183,157. The structure of nogalamycin can be shown as follows:

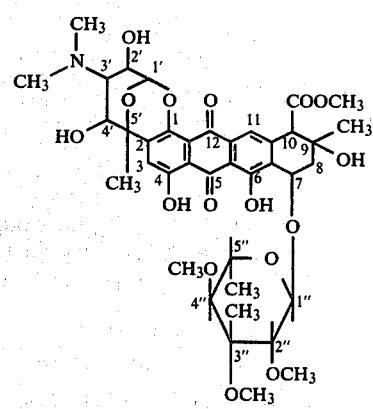

Antibiotics nogalarol and nogalarene, produced by acid hydrolysis of nogalamycin, and o-methylnogalarol, produced by acidic methanolysis of nogalamycin or nogalarol, are disclosed in U.S. Pat. No. 3,501,569.

Nogalamycinic acid is prepared by chemical modification of nogalamycin. The structure of nogalamycinic acid is as follows:

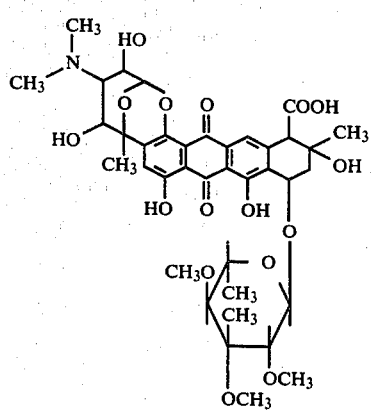

Nogalamycinic acid can be converted to nogamycin by contacting it with dimethylformamide. Nogamycin has the following structural formula:

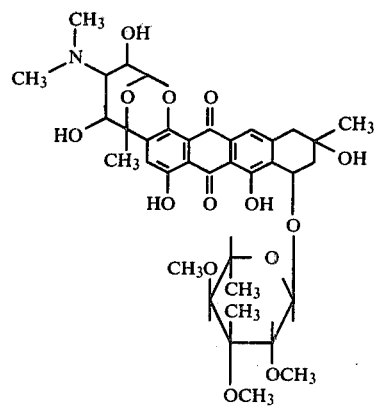

U.S. Pat. No. 4,086,245 concerns 7-O-alkylnogarols an their preparation from nogamycin. It is now known that these compounds are the (R) form and, that, also produced in the process, but heretofore not recognized or recovered, are the compounds of the subject invention which are the (S) form. The compounds of U.S. Pat. No. 4,086,245 can be shown as follows:

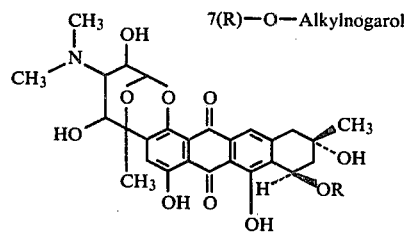

wherein R is an alkyl group of from 1 to 4 carbon atoms, inclusive.

BRIEF SUMMARY OF THE INVENTION

7(S)—O—Alkylnogarols can be prepared by acidic alcoholysis of nogamycin. For example, upon reacting nogamycin with methanolic hydrogen chloride at a temperature of about 50° C. to reflux, there is obtained 7(R)—O—methylnogarol (U-52,047) and 7(S)—O—methylnogarol (U-55,371). These compounds can be recovered from the reaction mixture by chromatographic means which effectively separate them into distinct entities.

7(S)—O—Alkylnogarol is biologically active and can be used in various environments to inhibit the growth of susceptible microorganisms. For example, 7(S)—O—alkylnogarol can be used for treating breeding places of silkworms, to prevent or minimize infections which are well known to be caused by *Bacillus subtilis*. Further, 7(S)—O—alkylnogarol can be used to minimize or prevent odor in fish and fish crates caused by contamination with *B. subtilis*. Also, 7(S)—O—alkylnogarol can be used to treat birds infected with *Mycobacterium avium*.

DETAILED DESCRIPTION OF THE INVENTION

The 7(S)—O—alkylnogarols of the subject invention can be shown by the following structure:

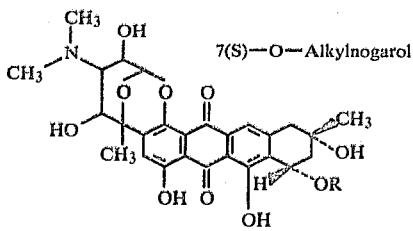

7(S)—O—Alkylnogarol wherein R is an alkyl group of from 1 to 4 carbon atoms, inclusive.

7(S)—O—Alkylnogarol can be prepared by acidic alcoholysis of nogamycin. The reaction can be conducted with a mineral acid ranging from about 0.05 N to about 1 N. Examples of acids which can be used are hydrogen chloride, hydrogen bromide, hydrogen iodide, sulfuric acid, phosphoric acid, and the like.

The reaction can be conducted at a temperature of about 50° C. to reflux. Reflux is preferred as lower temperatures prolong the completion of the reaction.

Suitable alcohols which can be used in the reaction are methanol, ethanol, propanol, isopropanol, n-butanol, and isobutanol.

The products can be recovered from the extract by chromatography on silica gel using the solvent system $CHCl_3$—$CH_3OH$ (95:5) which first removes the 7(R)—O—alkylnogarol produced in the reaction. The desired product, 7(S)—O—alkylnogarol, is then recovered from the reaction mixture by the use of a suitable solvent system, for example, $CHCl_3$—$CH_3OH$ (9:1).

7(S)—O—Alkylnogarol can be acylated under standard acylating conditions with an appropriate acid halide or anhydride to give the acylated compound. The acylation is carried out in the presence of an acid-binding agent. Suitable acid-binding agents include: amines such as pyridine, quinoline, and isoquinoline, and buffer salts such as sodium acetate. The preferred base is pyridine. Carboxylic acids suitable for acylation include (a) saturated or unsaturated, straight or branched chain aliphatic carboxylic acids, for example, acetic, propionic, butyric, isobutyric, tertbutylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic aliphatic carboxylic acids, for example, phenylacetic acid, phenylpropionic acid, phenylvaleric acid, cinnamic acid, phenylpropiolic acid, and naphthylacetic acid, and the like. Also, suitable halo-, nitro-, amino-, cyano-, and lower alkoxy- hydrocarbon carboxylic acids include hydrocarboncarboxylic acids as given above which are substituted by one or more of halogen, nitro, amino, cyano, or lower alkoxy, advantageously lower alkoxy of not more than six carbon atoms, for example, methoxy, ethoxy, propoxy, butoxy, amyloxy, hexyloxy groups and isomeric forms thereof. Examples of such substituted hydrocarbon carboxylic acids are:

mono-, di- and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
cyanopropionic acid;
ethoxyformic acid (ethyl hydrogen carbonate); and the like.

The acylated compounds, as described above, can be used in animals for the same biological purposes as disclosed above for 7(S)—O—alkylnogarol. For example, the acylated compounds can be given in oral form to an animal possessing the necessary enzyme to remove the acyl group, thus freeing the parent antibiotic compound which then inhibits susceptible bacteria.

Acid addition salts of 7(S)—O—alkylnogarol can be made by neutralizing the compound with an appropriate acid to below about pH 7.0, and advantageously to about pH 2 to pH 6. Suitable acids for this purpose include tartaric, glucuronic, and lactic which give water soluble salts, and hydrochloric, sulfuric, phosphoric, sulfamic, hydrobromic, and the like which give relatively water insoluble salts. Acid salts of 7(S)—O—alkylnogarol can be used for the same biological purposes as the parent compound.

7(S)—O—Methylnogarol has demonstrated antitumor activity against L1210 in vitro: $ID_{50}$ 0.13 mcg/ml; and P388 in vivo in mice: T/C 1.76 at 12.5 mg/kg. T/C is a value obtained by dividing the average length of life of test animals after infection by the average length of life of control animals.

The following examples are illustrative of the process and products of the invention, but are not to be construed as limiting. All percentages are by weight and all solvent mixture proportions are by volume unless otherwise noted.

Preparation Of Nogamycin

A solution of 12.3 g of nogalamycinic acid in a mixture of 20 ml of DMF and 50 ml of $CH_3OH$ was prepared by heating. After the solution had stood at room temperature overnight, it was put on 500 g of silica and eluted with $CHCl_3$—MeOH starting with 99:1 and gradually increasing the concentration of $CH_3OH$ until a ratio of 4:1 was reached. The elution was followed by thin layer chromatography (tlc) ($CHCl_3$—MeOH—$H_2O$; 78:20:2) and collecting those fractions containing only nogamycin (Rf 0.5). A total of 3.9 g was obtained. One and one-half grams was recrystallized from acetone-$CH_3OH$ (85:15). Obtained: 259 mg, mp 210°–215° C.; $a_D$ +273° (C 0.923, $CHCl_3$); uv (EtOH) λmax nm 236 (ε51,700), 259 (ε25,850), 290 (ε10,050) and 478 (ε16,100); ir (Nujol) 3500, 1670, 1630, 1575, 1295, 1230, 1110, 1055, 1005, 920, 890, 838, 778, 762 and 724 $cm^{-1}$; mass spectrum m/e 729; $^1$H NMR ($d_7$-DMF) 1.14, 1.23, 1.37, 1.69 (12 H, 4 $CH_3C$), δ2.07–2.38, 2.83–3.0 (m, 4 H, 2 $CH_2$), 2.42 [s, 6 H, $(CH_3)_2N$], δ3.13, 3.42, 3.52 (3 S, 9 H, 3 $CH_3O$), 3.3–4.2 (m, CHO, CHN), 4.95 (m, 1 H, benzylic CHO), δ5.32 (d, 1 H, anomeric), δ5.68 (1 H, anomeric) δ7.16, 7.32 (2s, 2 H, aromatic); $^{13}$C NMR ($CDCl_3$) δ15.2, 18.3, 24.2, 30.4 (4 $CH_3C$), 30.8 ($CH_2$), δ41.5 [$(CH_3)_2N$], δ44.1 ($CH_2$) δ48.7, 59.0, 61.4 (3 $CH_3O$), δ66.4–88.6 (CO and CN), δ96.79 and 99.81 (anomeric), δ113.1–161.4 (aromatic), δ179.7 and 190.8 (carbonyl). Anal. calcd. for $C_{37}H_{47}NO_{14}$: C, 60.96; H, 6.55; N, 1.92. Found: C, 58.55; H, 6.42; N, 1.94.

EXAMPLE 1-7(S)—O—METHYLNOGAROL

A solution of 50 g of nogamycin in 2 liters of $CH_3OH$ 0.55 N in HCl is stirred and heated under reflux for 4 hours. The solution is evaporated under reduced pressure to a volume of about 1 liter and 1.5 liter of $H_2O$ is added. The solution is extracted with two 500-ml portions of $CHCl_3$. The combined extracts are evaporated to dryness under reduced pressure. The residue is extracted with Skellysolve B leaving 8.2 g of red solid. This material is suspended in 150 ml of water which is adjusted to pH 7 with sodium hydroxide. The aqueous solution is extracted with $CHCl_3$ which is then evaporated to dryness leaving residue A.

The acidic solution which had been extracted with $CHCl_3$ is adjusted to pH 7 with 43 ml of 40% NaOH solution and extracted with 1 liter, 500 ml, and 300 ml of $CHCl_3$. The $CHCl_3$ extracts are combined and evaporated to dryness under reduced pressure leaving a residue which is chromatographed on 1.2 kg of silica gel using $CHCl_3$-$CH_3OH$ (95:5). After 10.5 liters of effluent has been collected, color begins to appear and 11 liters of effluent are retained and evaporated under reduced pressure to give 15.0 g of 7(R)—O—methylnogarol. The eluent is changed to $CHCl_3$-$CH_3OH$ (9:1) and, after 6 liters of effluent, a new colored fraction begins to appear. A 10-liter fraction is collected which is evaporated under reduced pressure to give 7.8 g of 7(S)—O—methylnogarol. This material is again treated with methanolic HCl as above. The material (residue B) obtained after neutralization and extraction is combined with residue A.

The combined material is chromatographed on 175 g of silica gel using $CHCl_3$-$CH_3OH$ (95:5). After 1 liter of effluent has been collected, 7(R)—O—methylnogarol begins to appear and 1.5 liters of effluent contains this material. After a further 300 ml, there is collected 2 liters of effluent which contains 7(S)—O—methylnogarol. Evaporation of this solution under reduced pressure gives 3.83 g of product. Three grams of this material is again chromatographed on 50 g of silica gel using $CHCl_3$—$CH_3OH$ (95:5) and collecting 10-ml fractions. Fractions 75–150 are combined on the basis of tlc analysis ($CHCl_3$—$CH_3OH$—$H_2O$; 78:20:2; Rf 0.52). Evaporation under reduced pressure gives 1.05 g of essentially pure 7(S)—O—methylnogarol; mp 184°–191° dec.; $[a]_D$480° (C 0.1305, $CHCl_3$); uv (EtOH) λmax nm 236 (ε49,750), 259.5 (ε24,050), 288 (ε9,250), 476 (ε15,400); ir (Nujol) 3400, 3200, 1660, 1620, 1575, 1285, 1220, 1120, 1095, 1055, and 1005 $cm^{-1}$; $^1$H NMR ($CDCl_3$+$CD_3OD$) δ1.43 (s, 3 H, $CH_3C$, C-9), 1.72 (s, 3 H, $CH_3C$, C-5'), 2.02, 2.12 (d of q, 2 H, H-8), 2.47 [s, 6 H, $(CH_3)_2N$], 2.77 (d, 1 H, H-10), 2.99 (d, 1 H, H-10), 3.33 (d of d, 1 H, H-3), 3.49 (s, 3 H, $CH_3O$), 3.58 (d, 1 H, H-3'), 4.04 (d of d, 1 H, H-2'), 4.76 (t, 1 H, H-7), 5.74 (d, 1 H, H-1'), 7.20 (s, 1 H, H-3), 7.21 (s, 1 H, H-11); $^{13}$C NMR ($CDCl_3$) δ23.9 (C-5'$CH_3$), 30.4 (C-9$CH_3$), 36.2 (C-8), 41.5 [$(CH_3)_2N$], 44.7 (C-10), 57.5 ($CH_3O$), 66.2 (C-3'), 71.3 (C-7), 69.8 (C-9), 70.4 (C-4'), 72.8 (C-2'), 75.0 (C-5'), 97.3 (C-1'), 113.2 (C-5a), 114.6 (C-12a), 116.7 (C-4a), 119.8 (C-11), 125.4 (C-3), 130.8 (C-6a), 133.0 (C-11a), 136.9 (C-2), 147.0 (C-10a), 147.5 (C-1), 155.8 (C-4), 161.2 (C-6), 180.1 (C-12), 190.8 (C-5); mass spectrum, M+ 541. Anal. calcd. for $C_{28}H_{31}NO_{10}$: C, 62.16; H, 5.78; N, 2.59. Found: C, 60.52; H, 5.89; N, 2.51.

| Antimicrobial Activity Of 7(S)—O—Methylnogarol | |
|---|---|
| Microorganism | Zone Size (mm) |
| Bacillus subtilis | 18 |
| Bacillus subtilis (synthetic medium)* | 11 |
| Bacillus cereus | 8 |
| Staphylococcus aureus | 0 |
| Streptococcus pyogenes | 18 |
| Sarcina lutea | 13 |
| Mycobacterium avium | 17 |
| Klebsiella pneumonia | 0 |

*Bacillus subtilis (synthetic medium) has the following composition:

| | |
|---|---|
| $Na_2HPO_4 \cdot 7H_2O$ | 1.7 g |
| $KH_2PO_4$ | 2.0 g |
| $(NH_4)_2SO_4$ | 1.0 g |
| $MgSO_4$ | 0.1 g |
| Glucose | 2.0 g |
| Bacto Agar[1] | 15.0 g |
| Distilled Water | 1 liter. |
| Metallic Ion Stock Solution[2] | 1 ml |

[1] Bacto Agar obtained from Difco Laboratories, Detroit, Michigan

[2] Metallic Ion Stock Solution consists of the following:

| | |
|---|---|
| $NaMoO_4 \cdot 2H_2O$ | 200 μg/ml |
| $CoCl_2$ | 100 μg/ml |
| $CuSO_4$ | 100 μg/ml |
| $MnSO_4$ | 2 mg/ml |
| $CaCl_2$ | 25 mg/ml |
| $FeCl_2 \cdot 4H_2O$ | 5 mg/ml |
| $ZnCl_2$** | 5 mg/ml |

**$ZnCl_2$ has to be dissolved separately using a drop of 0.1 N HCl for 10 ml of water. The stock solution is heated to bring all the compounds in solution, kept standing for 24 hours, and sterile filtered.

The above antimicrobial tests were run by dipping 6.35 mm filter paper discs into a 1 mg/ml solution of the test substance in methanol and placing the discs on agar plates containing a 1.3 mm layer of agar freshly seeded with the test organism. Discs dipped in methanol alone gave no inhibition zones. The plates were incubated 18 to 24 hours at 37° C. before reading the zones.

EXAMPLE 2-7(S)—O—ETHYLNOGAROL

A solution of 2 g of nogamycin in 150 ml of absolute EtOH 0.093 N in HCl is heated under reflux for 8 hours. It is then stirred overnight at room temperature. About half of the EtOH is removed by evaporation under reduced pressure, and the remainder is diluted with 100 ml of H$_2$O. Extraction of the aqueous solution with three 100-ml portions of CHCl$_3$, combination and evaporation under reduced pressure, gives 1.98 g of residue. This material is chromatographed by HPLC on 60 g of silica gel eluting with CHCl$_3$–CH$_3$OH (95:5) and collecting 150 fractions of 5 ml each. On the basis of tlc (CHCl$_3$-CH$_3$OH-H$_2$O; 78:20:2), fractions 17–36 are combined as pool 1 and fractions 110–145 as pool 2.

Pool 2 is evaporated under reduced pressure to give 0.32 g of essentially pure 7(S)-O-ethylnogarol; mp 172°–175° dec.; [α]$_D$ 487° (C 0.218, CHCl$_3$); Rf (CHCl$_3$-CH$_3$OH-H$_2$O; 78:20:2) 0.55; uv (EtOH) λmax nm 236 (ε43,700), 260 (ε22,300), 288$_{sh}$ (ε8,550), 476 (ε13,950); ir (Nujol) 3400, 3250sh, 3080, 1655, 1620, 1605, 1575, 1280, 1220, 1120, 1055, 1005 and 775 cm$^{-1}$; $^1$H NMR (CDCl$_3$) δ1.18 (t, 3 H, CH$_3$C), 1.38 (s, 3 H, CH$_3$C), 1.72 (s, 3 H, CH$_3$C), 2.04–2.24 (m, 2 H, H-8), 2.50 [s, 6 H, (CH$_3$)$_2$N], 2.68–4.25 (m, 9 H, CHO and CHN), 4.81 (m, 1 H, H-7), 5.74 (d, 1 H, H-1'), 7.19 (s, 2 H, H-3, H-11); $^{13}$C NMR (CDCl$_3$) δ15.7 (CH$_3$CH$_2$), 24.0 (CH$_3$C-5'), 30.5 (CH$_3$C-9), 42.0 (C-8), 41.5 [(CH$_3$)$_2$N], 44.6 (C-10), 65.1 (CH$_3$CH$_2$O), 66.1 (C-3'), 69.4 (C-7), 69.7 (C-9), 70.1 (C-4'), 72.7 (C-2'), 75.1 (C-5'), 97.1 (C-1), 113.1 (C-5a), 114.6 (C-4a), 116.5 (C-12a), 119.9 (C-11), 125.3 (C-3), 131.3 (C-6a), 132.9 (C-11a), 136.8 (C-2), 147.4 (C-10a), 147.6 (C-1), 155.6 (C-4), 161.2 (C-6), 180.1 (C-12), 190.7 (C-5); mass spectrum, M+ 555. Anal. calcd. for C$_{29}$H$_{33}$NO$_{10}$: C, 62.70; H, 5.95; N, 2.52. Found: C, 60.35; H, 5.93; N, 2.75.

EXAMPLE 3-7(S)-O-n-PROPYLNOGAROL

A solution of 5 g of nogamycin in 250 ml of n-propanol 0.14 N in HCl is heated under reflux for 2 hours. The solution is evaporated under reduced pressure to about one half its original volume and diluted with about 250 ml of water. This solution is extracted twice with CHCl$_3$. It is adjusted to pH 7 with sodium hydroxide. The neutralized solution is extracted several times with CHCl$_3$. The combined extracts are evaporated under reduced pressure to give 3.5 g of residue.

The residue is chromatographed on 200 g of silica gel eluting with CHCl$_3$-CH$_3$OH (95:5) and collecting 320 ten-ml fractions. The fractions are pooled on the basis of tlc analysis (CHCl$_3$-CH$_3$OH-H$_2$O; 78:20:2) as follows. Fractions 95–110 are combined as very good 7(R)-O-n-propylnogarol (Rf in the above solvent 0.69) and fractions 120–145 as somewhat poorer material. Combination and evaporation under reduced pressure gives, respectively, 173 mg and 0.64 g. Fractions 280–320 are combined and evaporated under reduced pressure to give 0.34 g of essentially pure 7(S)-O-n-propylnogarol. A portion of this is recrystallized from acetone to give material homogeneous by tlc in the above system (RF 0.57).

The properties of 7(S)—O—n-propylnogarol are as follows: mp 199°–212° dec.; [α]$_D$ 469° (C 0.16, CHCl$_3$); uv (EtOH) λmax nm 236 (ε44,950), 260 (ε23,050), 290 (ε8,700), 477 (ε14,500); ir (Nujol) 3440, 1660, 1620, 1575, 1290, 1220, 1115, 1095, 1055 and 1015 cm$^{-1}$; $^1$H NMR (CDCl$_3$) δ1.01 (t, 3 H, CH$_3$CH$_2$CH$_2$), 1.45 (s, 3 H, CH$_3$C), 1.78 (s, 3 H, CH$_3$C), 2.1-2.35 (m, 2 H, H-8), 2.58 [s, 6 H, (CH$_3$)N], 2.7–4.2 (m, 9 H, CHO and CHN), 4.83 (m, 1 H, H-7), 5.82 (d, 1 H, H-1'), 7.22 (s, 1 H, H-3), 7.26 (s, 1 H, H-11); $^{13}$C NMR (CDCl$_3$) δ10.9 (CH$_3$CH$_2$CH$_2$), 23.5 (CH$_3$CH$_2$CH$_2$), 24.0 (CH$_3$C-5'), 30.5 (CH$_3$C-9), 41.8 [(CH$_3$)$_2$N], 41.8 (C-8), 44.6 (C-10), 66.1 (C-3'), 69.8 (C-7), 69.8 (C-9), 70.1 (C-4'), 71.8 (CH$_3$CH$_2$CH$_2$O), 72.7 (C-2'), 75.0 (C-5'), 97.2 (C-1'), 113.1 (C-5a), 114.5 (C-4a), 116.6 (C-12a), 119.8 (C-11), 125.3 (C-3), 131.3 (C-6a), 132.8 (C-11a), 136.8 (C-2), 147.1 (C-10a), 147.4 (C-1), 155.7 (C-4), 161.3 (C-6), 180.0 (C-12 ), 190.5 (C-5); mass spectrum, M+ 569. Anal. calcd. for C$_{30}$H$_{35}$NO$_{10}$: C, 63.25; H, 6.15; N, 2.46. Found: C, 58.7; H, 5.83; N, 2.14.

EXAMPLE 4

By substituting the following alcohols in Example 1 for methanol, there is obtained the corresponding essentially pure 7(S)—O—alkylnogarols: isopropanol, n-butanol, and isobutanol.

We claim:

1. Essentially pure 7(S)—O—alkylnogarol, a compound having the following structure:

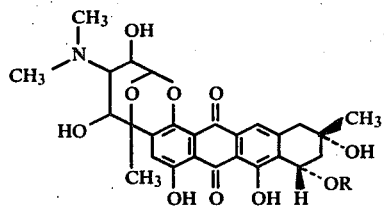

wherein R is alkyl of from 1 to 4 carbon atoms, inclusive.

2. Biologically acceptable acid addition salts of the compound of claim 1.

3. 7(S)—O—Methylnogarol, a compound according to claim 1, wherein R is methyl.

4. 7(S)—O—Ethylnogarol, a compound according to claim 1, wherein R is ethyl.

5. 7(S)—O—Propylnogarol, a compound according to claim 1, wherein R is propyl.

6. Acylates of 7(S)—O—alkylnogarol wherein said acyl group consists of hydrocarbon carboxylic acid acyl of from 2 to 18 carbon atoms, inclusive; halo-, nitro-, amino-, cyano-, and lower alkoxy-substituted hydrocarbon carboxylic acid acyl of from 2 to 18 carbon atoms, inclusive.

* * * * *